(12) United States Patent
Al Shehri

(10) Patent No.: US 10,441,384 B2
(45) Date of Patent: Oct. 15, 2019

(54) ENDODONTIC APICAL PLUG

(71) Applicant: Mohammed Al Shehri, Riyadh (SA)

(72) Inventor: Mohammed Al Shehri, Riyadh (SA)

( * ) Notice: Subject to any disclaimer, the term of this patent is extended or adjusted under 35 U.S.C. 154(b) by 13 days.

(21) Appl. No.: 15/509,494

(22) PCT Filed: Oct. 22, 2014

(86) PCT No.: PCT/IB2014/065534
§ 371 (c)(1),
(2) Date: Mar. 8, 2017

(87) PCT Pub. No.: WO2016/063110
PCT Pub. Date: Apr. 28, 2016

(65) Prior Publication Data
US 2017/0360530 A1    Dec. 21, 2017

(30) Foreign Application Priority Data
Sep. 24, 2014   (SA) .................................. 114350757

(51) Int. Cl.
*A61C 5/50* (2017.01)
*A61C 5/55* (2017.01)

(52) U.S. Cl.
CPC . *A61C 5/50* (2017.02); *A61C 5/55* (2017.02)

(58) Field of Classification Search
CPC .... A61C 5/50; A61C 5/62; A61C 5/40; A61C 5/35; A61C 5/55; A61C 5/60; A61C 5/70;
(Continued)

(56) References Cited

U.S. PATENT DOCUMENTS

| 430,522 | A | * | 6/1890 | Genese | ................. | A61C 13/30 |
| | | | | | | 433/221 |
| 3,863,345 | A | * | 2/1975 | Malmin | ................... | A61C 5/50 |
| | | | | | | 219/229 |

(Continued)

FOREIGN PATENT DOCUMENTS

| DE | 4011568 A1 | 10/1991 |
| EP | 1001728 B1 | 2/2008 |

(Continued)

OTHER PUBLICATIONS

International Search Report of the EPO, dated May 29, 2015.

*Primary Examiner* — Wade Miles
*Assistant Examiner* — Shannel N Wright
(74) *Attorney, Agent, or Firm* — Pathshegen IP LLC; Moshe Pinchas

(57) ABSTRACT

There is provided an endodontic apical plug including a wall, an open base and a closed tip, wherein the wall defines a longitudinal cavity extending from the open base of the plug to the closed tip of the plug. A width of the longitudinal cavity is greater at the open base of the plug and narrower towards the closed tip of the plug, the longitudinal cavity being configured to accept an injection tube connected to the injection device for filling the plug towards a root of a tooth. The longitudinal cavity comprises at least one lateral longitudinal opening in the wall of the plug, the at least one lateral opening being configured to, in use, enable a tooth filling material to pass through the at least one longitudinal opening and into a tooth.

14 Claims, 4 Drawing Sheets

(58) Field of Classification Search
CPC ....... A61C 13/30; A61C 13/225; A61C 8/016; A61C 8/0036; A61C 8/0045
USPC .......................................................... 433/224
See application file for complete search history.

(56) References Cited

U.S. PATENT DOCUMENTS

| | | | | |
|---|---|---|---|---|
| 3,899,830 A * | 8/1975 | Malmin | ................... | A61C 5/50 433/224 |
| 3,908,270 A * | 9/1975 | Fishman | ................... | A61C 5/50 433/224 |
| 3,919,774 A * | 11/1975 | Fishman | ................ | A61C 13/30 433/224 |
| 3,919,775 A * | 11/1975 | Malmin | ................... | A61C 3/00 433/32 |
| 4,384,852 A * | 5/1983 | Yamauchi | ............. | A61M 27/00 433/81 |
| 4,480,996 A * | 11/1984 | Crovatto | ................. | A61C 5/50 433/164 |
| 4,846,685 A * | 7/1989 | Martin | ................... | A61C 13/30 433/221 |
| 4,894,011 A * | 1/1990 | Johnson | ................... | A61C 5/50 433/81 |
| 5,051,093 A * | 9/1991 | Fitzmorris | ............... | A61C 5/50 433/224 |
| 5,085,586 A * | 2/1992 | Johnson | ................. | A61C 13/30 433/165 |
| 5,165,893 A * | 11/1992 | Thompson | ............... | A61C 5/50 433/224 |
| 5,833,457 A * | 11/1998 | Johnson | ................. | A61C 13/30 433/81 |
| 5,842,861 A * | 12/1998 | Buchanan | ................ | A61C 5/42 433/102 |
| 5,873,725 A * | 2/1999 | Perler | .................... | A61C 13/30 433/220 |
| 6,371,763 B1 | 4/2002 | Sicurelli, Jr. | | |
| 8,808,002 B2 * | 8/2014 | Simons | .................... | A61C 5/55 433/224 |
| 2004/0142301 A1 * | 7/2004 | Maissami | ............. | A61C 3/005 433/89 |
| 2005/0069836 A1 * | 3/2005 | Jia | ........................ | A61K 6/0038 433/81 |
| 2007/0225658 A1 * | 9/2007 | Jensen | ..................... | A61Q 5/62 604/212 |
| 2008/0171306 A1 * | 7/2008 | Goldberg | ............... | C08G 61/02 433/220 |
| 2008/0199832 A1 * | 8/2008 | Mannschedel | ....... | A61K 6/0073 433/224 |
| 2008/0299513 A1 * | 12/2008 | Jia | ........................ | A61K 6/0038 433/81 |
| 2010/0167232 A1 * | 7/2010 | Karmaker | ................ | A61C 5/50 433/81 |
| 2011/0129788 A1 * | 6/2011 | Lu | .......................... | A61C 13/30 433/29 |
| 2011/0217669 A1 | 9/2011 | Buchanan | | |
| 2014/0106299 A1 * | 4/2014 | Walter | ..................... | A61Q 5/04 433/90 |

FOREIGN PATENT DOCUMENTS

| | | | | |
|---|---|---|---|---|
| WO | WO-9307829 A1 * | 4/1993 | ............. | A61C 13/30 |
| WO | 2011161530 A1 | 12/2011 | | |
| WO | WO 2014060985 A2 * | 4/2014 | ............. | A61C 17/02 |

* cited by examiner

ENDODONTIC APICAL PLUG

INVENTION BACKGROUND

This invention is related to a tooth canal filler used for filling tooth root canals after extracting the nerve and preparing the canal for a final root filling status.

There are several previous experiments and inventions that have existed to achieve this goal, including Thermafil®, a canal filling method with European patent No. EP 1001728 B1. It requires heating the canal filler in advance prior to putting it in the canal in order to be mild. This causes an increase in tissue temperature to an extent that could harm it. Additionally, the material coating the filler may separate from it during the insertion process, which may harm the distribution of the leak-proof material inside the root canal; in addition to the problem arising from the need to remove the gripping part after the clinical procedure is performed.

EU patent application No. EP 2015109 A1 presented another canal filler. The problem with this system is that the leak-proof material coating the filler cannot interpenetrate and have the complex shape of canals. Therefore, there is a possibility of bacterial infiltration into such spaces. There is also the problem of the need to remove the gripping part after the clinical procedure.

US patent application No. US 2001/0217669 A1 presented a canal filler with no measurement scale on the filler gripping part and protrusions in the head of the filler that stop it inside the canal. Still, there exists the problem of heating the filler, the probable separation of the leak-proof material from the filler during insertion into canals, and the need to remove the gripping part after the clinical procedure is conducted.

KSA patent application No. 3335 is the closest application to the present one; however, there are several problems in the design of this filler. This includes the problem of designing the filler's cap with no supports that prevent it from going in the opposite direction, especially when the needle used in injecting the canal filling material is taken out. Additionally, there are no leak-proof means to prevent the leak in the filler cap, and designing the lateral openings in the shape of a teardrop makes the flow of canal filling material difficult, and its triangular-shaped (elliptical) top part of it is difficult to make. It being short makes the flow of canal filling material difficult as well. As for the presence of guiding wings it being continuous, this causes two problems. First, it hinders movement and flow of canal filling material because it divides the endodontic apical plug into three separate sections within a very small space. Second, it reduces flexibility of the carrier to bend, especially considering that most root canals have a curvature to some degree in the endodontic apex. Additionally, there is no place where the needle used in injecting the canal filling material meets the filler, as the reliance is on the friction between them, which may cause the filler to come out when taking the needle for injecting the filling material out.

GENERAL DESCRIPTION OF THE INVENTION

This invention is a plastic plug made of plastic or any other biocompatible material. It is put in the tooth root after extracting the nerve and prepare it for this filling. It has a central, cylindrical, longitudinal cavity with big symmetrical lateral elliptical openings and consecutively discontinuous guiding wings.

One of the advantages of this invention is that it does not need a gripping part like previous inventions that had the problem of their removal during filling or in case there is a need for a post inside the root to support fixed prosthodontics, because moving the gripping part and the surrounding filling harms the quality of the filling and may cause it to come out from its place. Additionally, the driller may change its direction inside the root because of the gripping part, which may cause a side hole in the canal wall. Also, the design of the current filler has a place to meet with the needle used in injecting the canal filling material, which the filler depends on when transferred into the root, such as (system B®, obtura II®, obtura III®, and HotShot®), with no need for any additional complex devices. One unique advantage of the invention is that the filler is not heated outside the canal, which eliminates the risk of harming tissue due to high temperature. Additionally, injecting the leak-proof material is done after inserting the filler into its final position inside the root. This also eliminates the risk of separation of the leak-proof material from the filler and gives it an opportunity to better take the shape of the canal. In addition to the unique design of the filler's cap, which has a double leak-proof cap, the design has two consecutive supports in the cap with an external angle of 45 degrees and an internal angle of 90 degrees that help prevent the leakage of the root filling material outside the canal. It serves as an inhibitor that fixes the carrier in its position in case the needle used in injecting the canal filling material is taken out. The presence of guiding wings with consecutively discontinuous spaces that separate each wing into several protrusions help the filling permeate around the filler. This makes the space better filled and the filler—after cooling the canal filling material fixed inside the root without being easily extracted.

Additionally, these consecutive spaces in the wings increase the flexibility of the carrier and its ability to bend inside the root canal. Also, the upper parts of the lateral annexes of the wings have small rounded angles. This helps the filler or cap reach its final position, even in tortuous canals.

Also, another advantage is that the length of the cap or filler does not exceed 5 mm from the root apex, which facilitates placing a post in the remaining space in the canal. This solves the problem of having a gripping part in the previous inventions, which obstructs this step. Additionally, there is a place allocated where the needle used in injecting the filling material meets the filler. That makes its exit easier after placing the filler in its final position and injecting the filling material. There is also a double edge at the top of the filler that further ensures preventing the leakage of material and the possibility of making solely the filler cap from the same canal filling material. This means making the filler in its entirety from one material and the cap alone from the same canal filling material. This makes the filling better take the shape of the root cap.

Finally, the presence of a cylindrical, longitudinal cavity inside the filler facilitates repeating treatment if the endodontitis returns and there is a desire to remove it from the root canal because this cavity helps root treatment tools (dental file) to hold inside the cavity and pull the filler out.

BRIEF DESCRIPTION OF DRAWINGS

The invention and other additional advantages can be more clarified through the following detailed description that refer to the illustrative drawings in which drawings represent the following.

DETAILED DESCRIPTION

Figure 1:
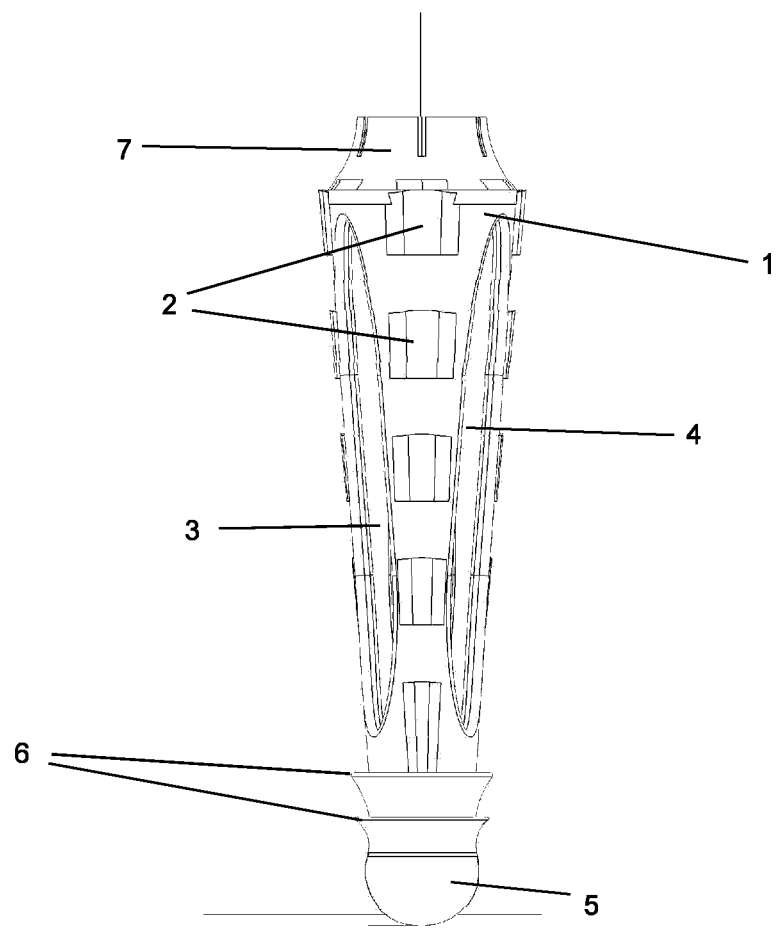
FIG. 1) a longitudinal section of the filler used in filling teeth root canals.

FIG. 1) illustrates a longitudinal section of the filler used in filling teeth root canals (1) made of plastic (or any other biocompatible material). This filler (1) that measures about 5 mm is placed inside the bottom of the tooth, and the remaining space is filled with filling material known in dentistry. The filler (1) is unique for its elliptical end (5) that allows it to be placed in the desired place, as the elliptical end (5) sets in the tooth apex to prevent leakage of filling material to jaw bones. The filler (1) has lateral openings (4) close to the elliptical end (5). Each opening (4) is linked to the longitudinal cavity (3) that reaches from top of the filler (1) (the opposite end of the elliptical end (5)) to the openings (3).

The filler (1) is linked from the outside to guiding wings (2) with consecutively discontinuous spaces that separate each wing into several protrusions, which helps the flow of the filling material into the filler (1) and better fill the place. Additionally, these consecutive distances in the wings (2) increase the flexibility of the filler and its ability to bend inside the root canal.

Figure 2:
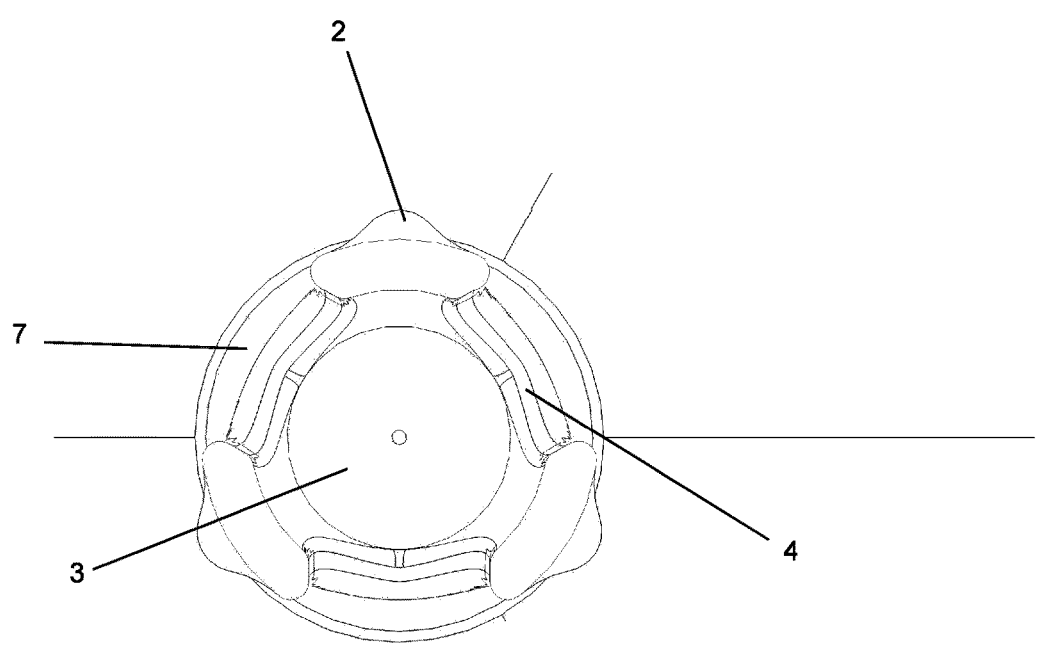
FIG. 2) a cross section of the filler used in filling teeth root canals from above.

FIG. 2) illustrates a cross-section of the filler used in filling teeth root canals from above. Round angles of the of guiding wings (2) are shown, in addition to the place designated for the needle used in injecting the canal filling material (7) and the longitudinal cavity (4) extending from the top of the filler (1) to the elliptical end (5).

Figure 3:
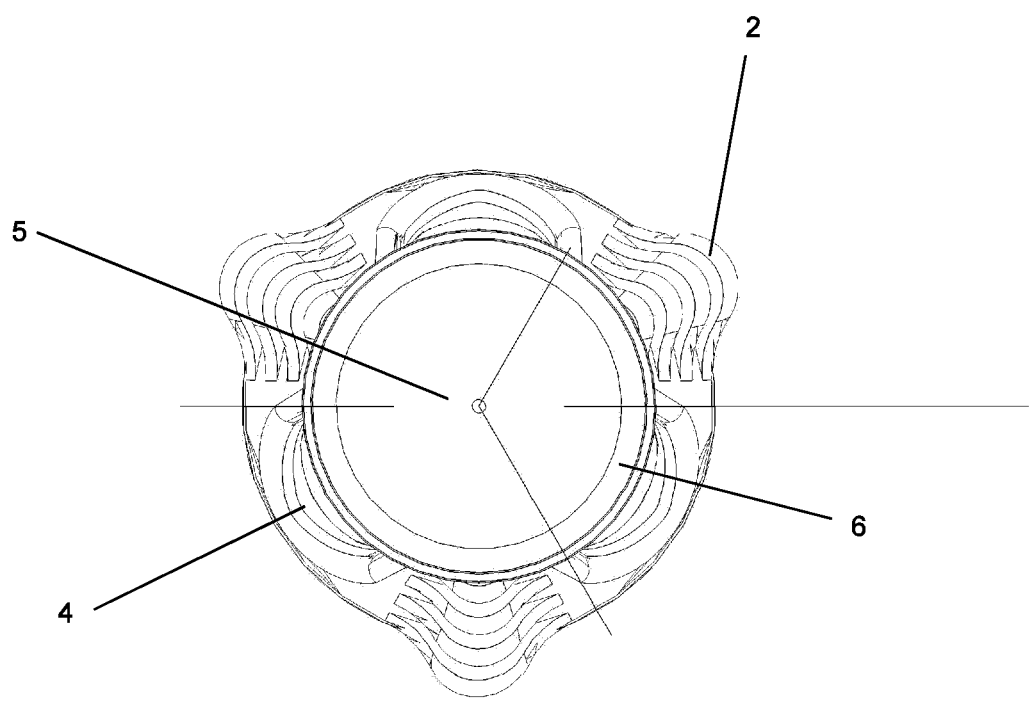
FIG. 3) a cross section of the filler used in filling teeth root canals from below.

FIG. 3) illustrates a cross-section of the filler used in filling teeth root canal from below. It shows the elliptical end (5) of the filler that can be made of the same material as that of the filler or can be made separately of the same material of the canal filler. There also appears the role of the double leak-proof cap (6).

Figure 4:
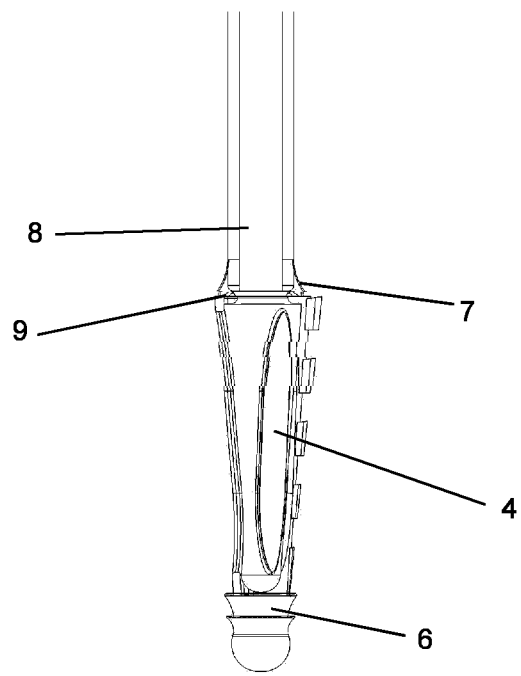
FIG. 4) the way the needle used in injecting the filling material meets with the filler and internal components.

FIG. 4) illustrates the way the needle used in injecting the filling material meets the filler and its internal components, in which the longitudinal cavity (3) is getting narrower when approaching the top end of the openings (9), as the injection tube stops directly right in its designated place (7).

Each one of the openings (4) has an elliptical shape, parallel in the middle. This design helps distributing the exit of filling material through the openings (4).

The work mechanism of the invention is inserting the injection tube (8) that is linked to the injection device (to inject the filling material later) through the longitudinal cavity (3) of the filler (1) until it completely stops going forward, directly at or before the top end of the openings (4) linked to the longitudinal cavity (3). Then the filler (1) is put at the canal (root) apex after extracting the nerve from it, by pushing it via the injection tube (8) connected to it (9) when the plug (1) is inserted into the root that is previously prepared for that. The filler (1) is directed downward and twisted, as the guiding wings (4) fill the root canals inside the tooth and guide the filler (1) when inserted and located (1) in the proper position inside the canal. Then the filling material is injected using the injection device (8) and the material goes out through the elliptical longitudinal openings (4), which guarantees that the pressure of the injected material is distributed from down upward.

It is worth mentioning that this filler (1) closes the root apex when injected, which prevents injection material from reaching tissues. It is known quite well that the filler (1) can be made of any convenient material. Often, it is made of plastic materials known in such technology. It can also be made of other more suitable materials determined later.

The invention claimed is:

1. An endodontic apical plug comprising: a side wall extending between an open base and a closed tip, wherein the wall defines a longitudinal cavity extending from the open base of the plug to the closed tip of the plug, wherein a width of the longitudinal cavity is greater at the open base of the plug and narrower towards the closed tip of the plug, the open base being configured for insertion therein an injection tube for inserting the plug towards a root of a tooth, and the longitudinal cavity being configured for injection therein, through the injection tube, tooth filling material; and wherein the side wall includes at least one lateral opening, wherein each lateral opening longitudinally extends along said side wall from said open base to said closed tip and being configured to distribute the tooth filling material from the longitudinal cavity into the root of the tooth said opening being configured such that the pressure of the tooth filling material is distributed from down upward.

2. The endodontic apical plug according to claim 1, wherein at least two lateral longitudinal openings are provided in the wall of the plug.

3. The endodontic apical plug according to claim 1, wherein at least three lateral longitudinal openings are provided in the wall of the plug.

4. The endodontic apical plug according to claim 1, wherein the lateral longitudinal openings have an elliptical shape.

5. The endodontic apical plug according to claim 1, wherein the closed tip of the plug is provided with an elliptical cross sectional shape.

6. The endodontic apical plug according to claim 1, wherein the closed tip of the plug is made of a material which is the same as a material in which the walls and open base are made of.

7. The endodontic apical plug according to claim 1, wherein the wall close to the closed tip of the plug is provided with a leak resistant cap portion comprising a first flange and a second flange.

8. The endodontic apical plug according to claim 1, wherein the open base is provided with double edge configured to prevent leakage and to aid connection of the injection tube to the open base.

9. The endodontic apical plug according to claim 1, wherein the injection tube is a needle.

10. The endodontic apical plug according to claim 1, wherein an outer surface of the wall is provided with at least one guiding wing configured for guiding the plug into the root of the tooth.

11. The endodontic apical plug according to claim 1, wherein the wall is provided with at least two guiding wings.

12. The endodontic apical plug according to claim 11, wherein the guiding wings are discontinuous guiding wings with spaces between each discontinuous portion of the guiding wing, and wherein the guiding wings do not cover any of the longitudinal openings.

13. The endodontic apical plug according to claim 11, wherein the cross-sectional profile of the guiding wing comprises a rounded shape.

14. A kit of parts comprising: an endodontic plug having a side wall extending between an open base and a closed tip, wherein the wall defines a longitudinal cavity extending from the open base of the plug to the closed tip of the plug, and an injection tube configured to be inserted inside said open base and for injection tooth filling material inside said longitudinal cavity; wherein a width of the longitudinal cavity is greater at the open base of the plug and narrower towards the closed tip of the plug, the open base being configured for insertion therein an injection tube for inserting the plug towards a root of a tooth, and the longitudinal cavity being configured for injection therein, through the injection tube, tooth filling material; and wherein the side wall includes at least one lateral opening, wherein each lateral opening longitudinally extends along said side wall from said open base to said closed tip and being configured to distribute the tooth filling material from the longitudinal cavity into the root of the tooth said opening being configured such that the pressure of the tooth filling material is distributed from down upward.

\* \* \* \* \*